United States Patent [19]

Discko, Jr.

[11] Patent Number: 5,001,803

[45] Date of Patent: Mar. 26, 1991

[54] DISPOSABLE DENTAL BRUSH

[76] Inventor: John Discko, Jr., 50 Laura Rd., Hamden, Conn. 06514

[21] Appl. No.: 325,888

[22] Filed: Mar. 20, 1989

[51] Int. Cl.⁵ .......................... A46B 5/02; A46B 9/04
[52] U.S. Cl. .................................. 15/167.1; 15/160; 15/166; 15/172; 604/1
[58] Field of Search .................. 15/167.1, 104 R, 201, 15/172, 144 R, 169, 172, 167.3, 184, 166, 160, 192; 128/62 A, 66; 132/308, 313, 317, 321, 329; 401/268; 433/141, 142, 217.1, 80; 604/1, 2, 3

[56] References Cited

U.S. PATENT DOCUMENTS

| | | | |
|---|---|---|---|
| 3,106,738 | 10/1963 | Bohne | 15/184 |
| 3,609,789 | 10/1971 | Slater | 15/172 |
| 4,712,266 | 12/1987 | Yamaki | 132/321 X |
| 4,731,896 | 3/1988 | de la Tour | 15/106 |
| 4,805,646 | 2/1989 | Shimenkov | 132/321 X |

Primary Examiner—Edward L. Roberts
Attorney, Agent, or Firm—Arthur T. Fattibene; Paul A. Fattibene

[57] ABSTRACT

A disposable dental brush for applying various dental materials onto a tooth in thin, even coatings, e.g. etchants, sealants, bonding agents, tints, opaquers, varnishes and the like that includes an elongated straight handle having a tuft of bristles connected to one end thereof. The elongated handle is constructed so as to allow the portion thereof adjacent to the brush end relative to the longitudinal axis of to be readily bent so as to angularly dispose the brush end the handle. The arrangement is such that the brush can be used either as a straight brush or an angularly bent brush to reach difficult areas of the mouth or teeth. Also, the brush is made of inexpensive plastic material so as to render it readily expendible or disposable after each use.

3 Claims, 3 Drawing Sheets

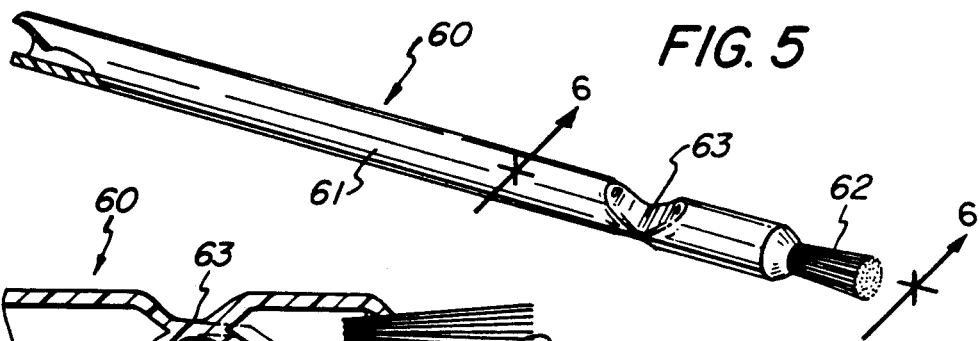
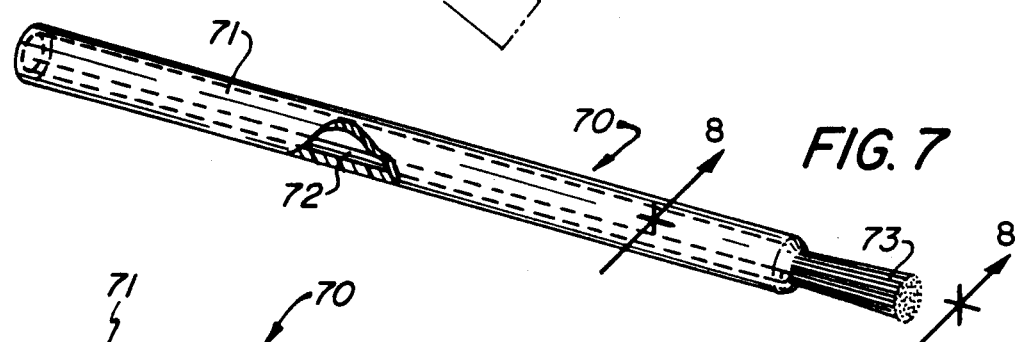
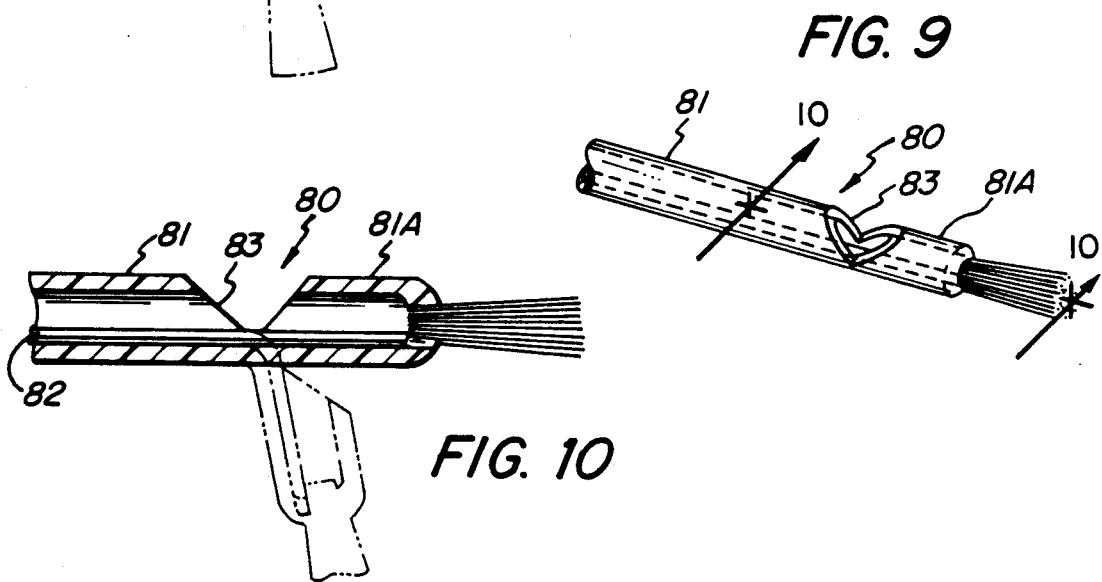

DISPOSABLE DENTAL BRUSH

FIELD OF INVENTION

This invention is directed to dental brushes for applying various dental materials to a tooth structure in thin, uniform coatings.

PROBLEM AND PRIOR ART

Various types of paint brushes are readily known. Included in the known paint brushes are artist brushes which comprise an elongated handle having a plurality of bristles or brush hairs connected to one end. The known paint brushes are generally not intended to be rendered readily disposable. As a consequence, such brushes are required to be cleaned and maintained between uses.

Heretofore, such brushes have been minutized for use in dentistry as many dental procedures require various dental materials, such as sealants, bonding agents and the like, to be painted onto a tooth in thin, even coatings or layers. However, because of the need for sterilization to prevent cross-contamination between patients, the use of miniature paint brushes required frequent cleaning. Because the dental materials in current use include various materials that cure in a relatively short period, cleaning and/or sterilization of such brushes was frequently impossible. With the advent of AIDS, contagious hepatitis and other communicable diseases and the quick setting dental materials, a disposable brush is desirable.

A known disposable dental type brush comprised a resuable handle portion that included a fixed angular end portion to which a disposable tuft of bristles was detachably connected. While the bristles or tuft of bristles was rendered readily disposable after each use, the handle, being a reusable component, had to be sterilized between patients to ensure against cross-contamination. Such known reusable brush construction with detachable bristles is relatively expensive. Also, it invariably happens that after several uses, the dental materials would tend to accummulate onto the reusable handle portion to result in a time-consuming cleaning problem. Such known reusable brush handles had another noted disadvantage in that they were not well suited for use on anterior teeth, due to the fixed angular offset of the brush end. Thus, while the angular offset, reusable handle with disposable brush heads solved some of the problems with which a dentist is confronted, it did not solve all of the problems involved in painting dental materials onto a tooth structure, as the reusable handle still required cleaning and sterilization between patients. Also, the fixed angular offset brush end rendered the use thereof inconvenient when working in certain areas of the mouth.

Another disadvantage noted with the dental brushes having a reusable handle was that the disposable brush tips often did not fit well to the end of the handle and caused such brush tips to fall out if too loose, or difficult to insert if too tight, as it was difficult to maintain the tolerances of the disposable brush ends.

Another reusable dentist brush, such as manufactured by or for L.D. Caulk, a division of Dentsply International, consisted of an artist type brush in which the brush tufts were held in place onto the end of a handle by a crimped metal collar. The metal collar was prebent to a fixed angle. Such brushes are relatively expensive and were intended to be cleaned after each use and re-used. To facilitate the cleaning thereof, the manufacturer would include a bottle of solvent for cleaning such brushes. Also, the pre-fixed angle brush was limited to the extent it was not convenient for use on anterior teeth for which a straight brush was more appropriate. Also, the fixed angle was not optimal for all hard to reach areas of the mouth.

OBJECTS

An object of this invention is to provide a readily inexpensive dental brush that is rendered totally disposable after each use.

Another object of this invention is to provide a dental brush having a bendable end portion whereby the brush end can be optionally disposed and maintained in variously fixed angular relationships relative to the longitudinal axis of the brush handle.

Another object of this invention is to provide a dental brush that is relatively simple in construction, positive in operation and inexpensive to manufacture.

Another object is to provide a dental brush wherein the brush end can be readily adjusted by the dentist to enable the dentist to work in all areas of the mouth with the optimum ease and convenience.

Another object is to provide a dental brush having a flexible or bendable brush end that is integrally constructed as a unitary unit.

SUMMARY OF THE INVENTION

The foregoing objects and other features and advantages are obtained by a dental brush having a generally elongated handle portion preferably made of an inexpensive material, e.g., a suitable plastic, whereby the entire brush can be rendered readily expendible after each use. Connected to one end of the brush is the brush tip which generally comprises a tuft of bristles suitably secured to one end of the handle portion. In accordance with this invention, the handle portion is provided with a flexible or hinge construction located adjacent the brush end, whereby the brush end can be optionally bent so that the brush end can be bent or flexed between an axially aligned position relative to the longitudinal axis of the handle portion to various predetermined offset angular positions relative to the longitudinal axis of the handle portion so as to facilitate access to hard to reach areas. The flexed or bent portion of the handle is constructed so that the angular offset is maintained in the adjusted bent position. In one form of the invention, the flexing or bendable portion is integrally formed of the same material used for making the brush handle portion and functions as a living hinge. In another form of the invention, the flexible or bendable portion may be formed by a wire connected to the handle portion. In another form of the invention, the handle portion may be provided with a plurality of bendable portions intermediate the ends thereof to enable the brush end to be offset or angularly disposed in a compound angular relationship.

FEATURES

A feature of this invention resides in the provision of a totally expendible dental brush whereby the brush end can be optionally disposed between an axial aligned position to a variety of predetermined angularly offset positions relative to the longitudinal axis of the handle portion.

Another feature resides in the provision wherein the flexible portion of the brush is integrally formed as a portion of the handle portion.

Another feature of this invention is to provide the handle portion of the brush with more than one bendable or flexible portion whereby the brush end can be disposed at a compound angle relative to the longitudinal axis of the brush.

Other features and advantages will become readily apparent when considered in view of the drawings and detailed description thereof, wherein FIG. 1 is a perspective view of a disposable dental brush embodying the invention.

FIG. 2 is a modified embodiment of the invention.

FIG. 3 comprises still another modified embodiment of the invention.

FIG. 5 is another modified embodiment.

FIG. 6 is a fragmentary sectional view taken along line 6—6 on FIG. 5.

FIG. 7 is a perspective view of another modified embodiment having a portion broken away.

FIG. 8 is a section view taken along line 8—8 on FIG. 7.

FIG. 9 is a fragmentary perspective view of another modification.

FIG. 10 is a section view taken along line 10—10 on FIG. 9.

DETAIL DESCRIPTION

Figure 1:
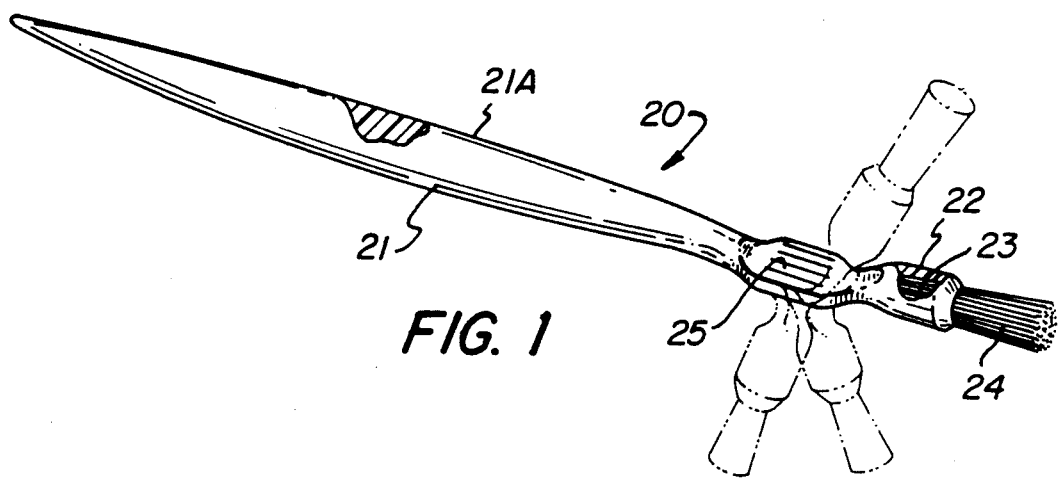

Referring to the drawings, there are illustrated various embodiments of a disposable dental brush embodying the invention. In dentistry, there are a host of procedures that require a dentist to paint onto the tooth structure of a patient various dental material such as sealants, bonding agents, tints, opaquers, varnishes and other liquid type materials in thin, even coatings or layers. Such procedures are of particular importance in cosmetic dentistry and in preventive dentistry, e.g. placing sealants on children's teeth. To avoid tedious problems of cleaning such brushes and to minimize cross-contamination of patients, the present invention is directed to a totally disposable dental brush that is rendered readily expendible after each use. Referring to the drawing, there is shown in FIG. 1, one of the preferred forms of the invention. As shown, the disposable dental brush 20 of FIG. 1 comprises a handle portion 21 which is formed of a suitable inexpensive material, e.g. a suitable plastic that can be readily molded as an integral unit. The illustrated brush handle 21 comprises an elongated handle portion which is shaped intermediate the ends thereof with a thickened portion as indicated at 21A, which tapers inwardly toward the opposed ends thereof, so as to provide a gripping portion to give the dentist a comfortable and controllable grip on the brush. The brush end 22 of the handle portion is provided with a bore 23 to provide a seat for receiving a tuft of bristles 24. The tuft of bristles are fixedly secure within the seat defined by bore 23, e.g. by a staple or adhesive or by another other suitable means.

In accordance with this invention, the handle portion adjacent the brush end 22 is provided with a hinging means whereby the brush end can be readily bent relative to the longitudinal axis of the handle portion 21. As shown in FIG. 1, the hinging means comprises a flattened hinge section 25 which defines a reduced section between the handle portion 21A and the brush end 22 which is integrally formed of the material from which the handle portion is formed. The reduced or flattened section 25 is sufficiently rigid so as to maintain the brush end 22 co-axially disposed relative to the longitudinal axis of the handle portion, so that the brush 20 may be used by the dentist as a straight brush when working on anterior teeth. The reduced or bendable portion 25 is also sufficiently flexible so as to permit the dentist to angularly offset the brush end 22 relative to the longitudinal axis of the handle portion 21 as shown in the various dotted line positions. The arrangement is such that the dentist or user can bend the brush end to any predetermined angular position that may be necessary to reach difficult areas of the mouth, e.g. the most rear posterior teeth. Also, the arrangement is such that the material from which the brush is formed will maintain the adjusted position of the brush end 22. Thus, the flexible portion 25 functions as a hinge between the gripping portion 21A of the handle and the brush end 22 of the brush and will securely retain the brush end in the adjusted position thereof. With a single brush as described, a dentist can reach all areas of the mouth in a simple and convenient manner, and which brush will enable the dentist to coat in even layers any tooth with ease and comfort for both dentist and patient. After use, the entire brush is disposed of; thus eliminating completely the need for any clean up and/or sterilization to guard against cross-contamination between patients, which has been an age-old problem in dentistry.

Figure 2:
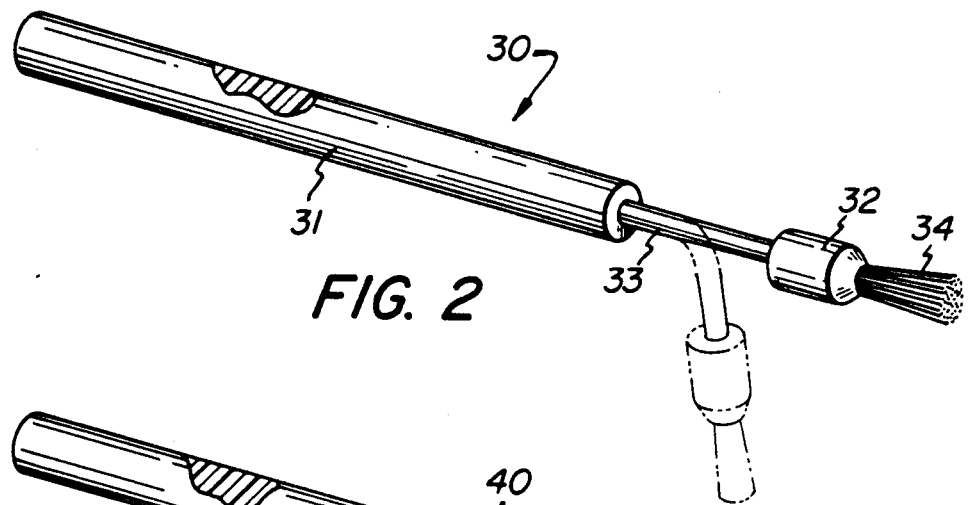

FIG. 2 illustrates another modification of the invention. In this form of the invention, the dental brush 30 comprises a handle portion 31 connected to the brush end 32 by a reduced section 33 having a rod like configuration or circular cross-section. The tuft of bristles 34 is secured to the brush end 32 in a manner hereinbefore described. In this form of the invention, the reduced section 33 is integrally formed with the handle portion 31 and brush end 34 and made of the same material. The reduced portion 33 is rendered sufficiently flexible for angularly disposing the brush end 32 relative to the longitudinal axis of the handle portion 31. In this form of the invention, it will be noted that the brush end 32 can be bent at any angle within a 360° radius about the longitudinal axis of the brush handle 31. As described with respect to FIG. 1, the nature of the material of the reduced or hinge section 33 is such that it will maintain the brush end 32 in the adjusted position. Also, the brush 30 can be readily used by the dentist as a straight brush or as an angularly disposed brush, thereby allowing the dentist the flexibility to reach all areas of the mouth. It too is rendered readily disposable after use.

Figure 3:
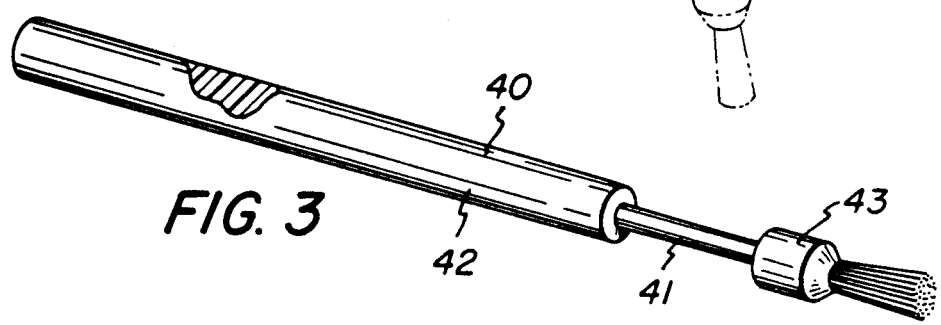

FIG. 3 illustrates an embodiment similar to that of FIG. 2, except that the brush 40 has a reduced hinge section 41 which comprises a length of wire-like material which may be made of a flexible metal or rod. In this form, the rod 41 is fixedly connected to and between the handle portion 42 and the brush end 43 by suitable means. In all other respects the construction and operation is similar to that herein described with respect to FIG. 2.

Figure 4:
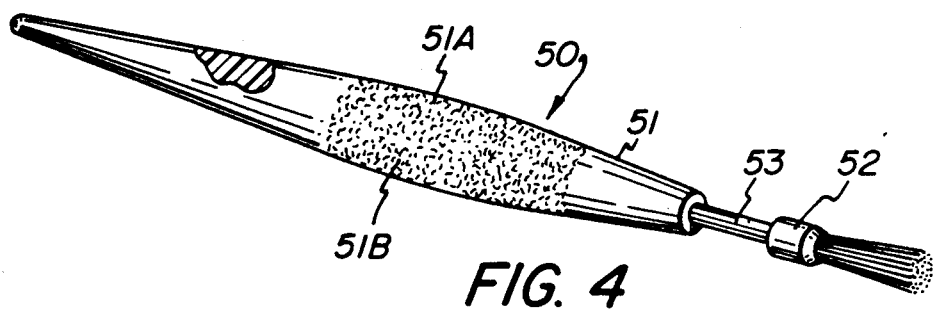
FIG. 4 is another modified embodiment of the invention.

FIG. 4 illustrates a brush construction 50 in which the handle portion 51 is formed with a bluging center portion as indicated at 51A that tapers inwardly toward the opposed ends thereof. The intermediate portion of the handle portion 51 is provided with a slightly roughened surface 51B to facilitate the gripping thereof. The hinge means 53 between the handle portion 51 and the brush end portion 52 may be formed as described in either FIGS. 2 or 3. In all other respects, the brush 50 is similar to that hereinbefore described.

FIGS. 5 and 6 illustrate still another modification embodying the invention. As shown in FIGS. 5 and 6, the brush 60 includes a handle portion 61, which is formed of a tubular disposable plastic material of a predetermined length. In this form of the invention, a tuft of bristles 62 is suitably inserted into and secured in one end of the tubular handle portion 61. Intermediate the handle portion and adjacent to the brush end 62, the handle porton is compressed to define a flexible hinge section 63. Thus, as shown in FIG. 6, the brush end can be readily flexed and angularly disposed relative to the longitudinal axis of the brush 60 in a manner hereinbefore described. In this form, the hinge section 63 is sufficiently rigid to permit the dentist to use the brush as a straight brush as shown in FIG. 5 or as a bent brush as shown in FIG. 6.

FIGS. 7 and 8 illustrate another modified form of the invention. In this form of the invention, the brush 70 is provided with a brush handle 71 which may be made of a material which may not have a memory or the ability to maintain a bent or angular position, e.g. tubular paper or other inexpensive material incapable of maintaining a bent position. In this arrangement, a length of bendable wire 72 extends longitudinally along the length of the handle portion 71, and is suitably secured thereto. In the construction described, the brush end can be bent relative to the longitudinal axis of the brush and maintained in the angular adjusted position by the flexibility of the wire 72. It will be understood that the tuft of bristles 73 is inserted and secured to the end of the handle portion 71 in a manner similar to that hereinbefore described. Thus, the construction of FIGS. 7 and 8 also allows a dentist to use the brush 70 as either a straight brush or a bent brush that is also readily expendible after each use thereof.

FIGS. 9 and 10 illustrate a slightly modified variation of the embodiment disclosed and described with respect to FIGS. 7 and 8. In this form of the invention, the handle portion 81 of brush 80 is also formed of a tubular handle portion having a length of flexible wire 82 extending therealong as described in FIGS. 7 and 8. However, to facilitate the flexing or bending of the brush end portion 81A, the handle portion is provided with a notched out area 83 in the area bout which the brush end is adapted to be bent. In this form of the invention, the brush end 81A can be variably flexed in one direction through approximately 180° and in the opposite direction a limited amount depending upon the angulation of the notched out area. In all other respects, the construction of FIGS. 9 and 10 is similar to that hereinbefore described.

Figure 11:
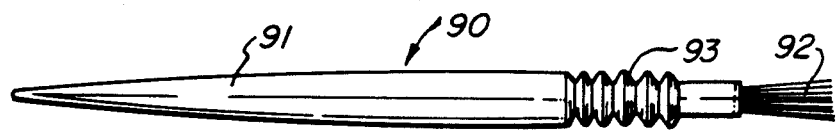
FIG. 11 illustrates another modified form of the invention wherein the hinging portion is defined by pleated folds.

FIG. 11 illustrates yet another modification of a disposable bendable type dental brush 90. In this form of the invention, the brush handle 91 is formed of a suitable plastic material having a tuft of bristles 92 defining the brush end suitably secured in one end thereof. The bendable portion comprises a pleated section 93 to define a plurality of accordian-like folds. The pleated section 93 is sufficiently rigid so that the brush 90 can be used as a straight brush, and which pleated section is sufficiently flexible so as to allow a dentist to angularly dispose the brush end relative to the longitudinal axis of the brush handle; whereby the adjusted angle is maintained until readjusted. From the foregoing, it will be noted that the dentist can regularly adjust the angular relationship to suit a particular working condition. The known dental brushes do not permit such adaptation.

Figure 13:
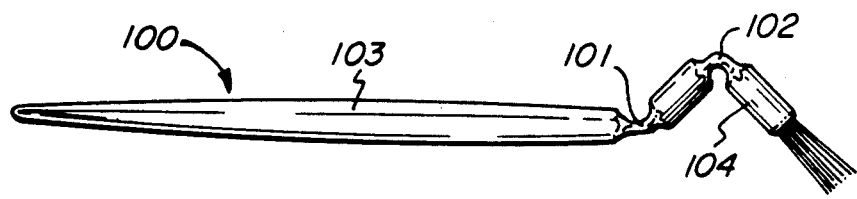
FIG. 13 illustrates the brush modification of FIG. 12 in its bent position.
Figure 12:
FIG. 12 illustrates a further modification illustrated as a straight brush.

FIGS. 12 and 13 illustrate still another form of the invention. The dental brush 100 of FIGS. 12 and 13 is similar to that described with respect to FIG. 1, except that brush 100 is provided with a plurality of bendable or flexible hinge sections 101 and 102, longitudinally spaced along the handle portion 103 adjacent the brush end 104. The construction of FIGS. 12 and 13 enables the dental brush to be bent at the two hinged sections 101 and 102 independently of each other to angularly dispose the brush end 104 at a compound angle relative to the longitudinal axis of the brush handle to provide the dentist with a greater degree of flexibility in reaching difficult or hard to reach areas. Such a compound bend is illustrated in FIG. 13. The multiple hinged portion provides for a "goose neck" type of adjustment for the brush end that will maintain the angularly disposed position of the brush. The rigidity and flexibility of the described constructions enables the brush to be used as a straight brush or as a multiple bend brush capable of access to the most difficult areas of the mouth, and which construction is suitable for making an economical brush that is sufficiently inexpensive so as to render it readily disposable after each use.

Figure 14:
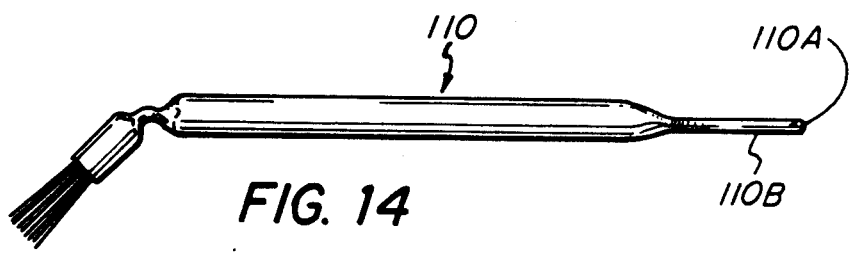
FIG. 14 is another brush modification.
Figure 15:
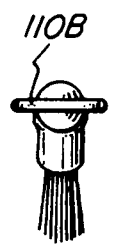
FIG. 15 is a detail end view of the brush of FIG. 14.

FIGS. 14 and 15 are directed to a further dental brush modification 110. Dental brush 110 differs from those previously described by providing at the free end 110A of the handle portion a flat end 110B to define a flat spatula end. Such spatula end can be utilized by the dentist to mix the ingredients of the material he desires to paint onto a patient's tooth. With the exception of the spatula end portion 110B, the dental brush proper may be formed in accordance to any of the described embodiments.

Figure 16:
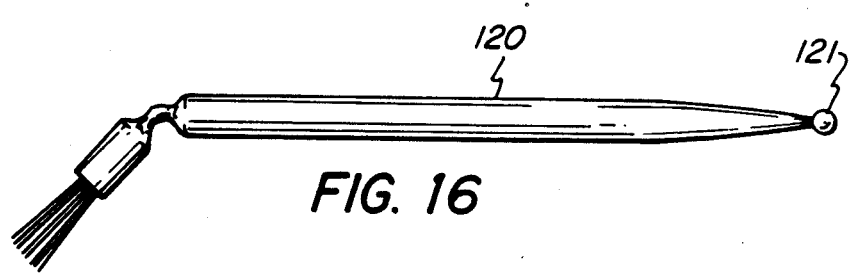
FIG. 16 is another brush modification.

FIG. 16 discloses a further modification, wherein the dental brush 120, which may be formed or constructed like any of the foregoing described modifications, is provided with a ball tip 121 at the free end of the handle portion, i.e., the end opposite the brush end. The ball tip 121 can be used as a packing ball by the dentist in those procedures requiring the dentist to pack or fill a tooth with dental material.

Figure 17:
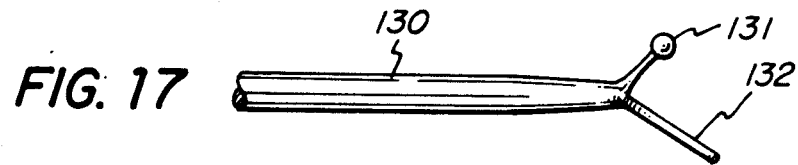
FIG. 17 is yet another brush modification embodying the invention.

FIG. 17 is a further modification of a dental brush wherein the free end of the brush handle 130 is provided with both a packing ball tip 131 as described in FIG. 14 and an angularly disposed flat spatula portion 132.

From the foregoing, it will be apparent that the described dental brushes can be readily fabricated of low cost material so as to render it economically feasible to render them totally expendable after each use. The described dental brushes also eliminate completely the clean up and/or sterilizing problems heretofore encountered in a dental office with the prior known dental brushes. There are no brush tips to be cleaned or changed. Cross-contamination is eliminated, and most importantly is the fact that the described brushes permit a dentist to use the same either as a straight brush or a bent brush to achieve any desired contra-angle necessary to maximize access to even the most difficult to reach areas of the mouth.

While the invention has been described with respect to particular embodiments thereof, it will be understood that variations and modifications may be made without departing from the spirit or scope of the invention.

What is claimed is:

1. A readily disposable dental brush for applying various dental materials to a tooth in thin, even coatings comprising
    an elongated tubular handle formed of a plastic material and having a continuous, uninterrupted bore extending therethrough,
    said bore opening to at least one of said handle,
    a tuft of bristles partially inserted into the open end of said bore, said tubular member allowing said tuft of bristles to be inserted therein to a selectable predetermined length,
    means for securing the bristles therein,
    said handle having a hinging section formed along said tubular handle spaced from said open end and adjacent said tuft of bristles adjacent the brush end of the handle, said hinging section being defined by the opposed tubular wall portions of said handle being disposed contiguous to one another to define a flattened portion, whereby said hinging section is rendered sufficiently rigid for allowing said handle to maintain its co-linear elongation for use as a straight brush and yet being sufficiently flexible to permit said brush end to be angularly disposed relative to the longitudinal axis of said elongated handle and said flattened portion imparting a memory to said tubular member to maintain said brush end in said angularly disposed position.

2. A readily disposable dental brush as defined in claim 1 wherein said tubular handle is round.

3. A readily disposable dental brush as defined in claim 1 wherein said hinged section permits said brush end to be variably angularly disposed relative to said handle through a range of 180°.

* * * * *

UNITED STATES PATENT AND TRADEMARK OFFICE
CERTIFICATE OF CORRECTION

PATENT NO.   : 5,001,803
DATED        : March 26, 1991
INVENTOR(S)  : John Discko, Jr. and William B. Dragan It is certified that error appears in the above-identified patent and that said Letters Patent is hereby corrected as shown below:

<u>Title page,</u>
Item [76], Inventor's, name and address "John Discko, Jr., 50 Laura Rd., Hamden, Conn. 06514" should read -- John Discko, Jr., Hamden, CT; William B. Dragan, Easton, CT --.

Signed and Sealed this

Twenty-seventh Day of January, 2004

JON W. DUDAS
*Acting Director of the United States Patent and Trademark Office*